United States Patent [19]

Yoshioka et al.

[11] Patent Number: 5,585,090

[45] Date of Patent: Dec. 17, 1996

[54] COSMETICS HAVING SUNSCREEN PROPERTIES

[75] Inventors: Takatsugu Yoshioka, Moriyama; Hisatoshi Masuda, Kusatsu; Hidekazu Tanaka, Youkaichi, all of Japan

[73] Assignee: The Procter & Gamble Company, Cincinnati, Ohio

[21] Appl. No.: 199,867

[22] Filed: Feb. 22, 1994

Related U.S. Application Data

[63] Continuation-in-part of Ser. No. 849,923, Mar. 12, 1992, abandoned.

[51] Int. Cl.$^6$ .............................. A61K 7/43; A61K 7/44
[52] U.S. Cl. .................................. 424/59; 424/60
[58] Field of Search ........................... 424/59, 60

[56] References Cited

U.S. PATENT DOCUMENTS

| | | | |
|---|---|---|---|
| 5,000,937 | 3/1991 | Grollier et al. | 424/47 |
| 5,009,969 | 4/1991 | Miller | 424/59 |
| 5,026,540 | 6/1991 | Dixon et al. | 424/60 |
| 5,028,417 | 7/1991 | Bhat et al. | 424/59 |
| 5,032,390 | 7/1991 | Iwaya et al. | 424/59 |
| 5,087,445 | 2/1992 | Haffey et al. | 424/59 |
| 5,223,250 | 6/1993 | Mitchell | 424/59 |
| 5,372,804 | 12/1994 | Khoshdel | 424/59 |

FOREIGN PATENT DOCUMENTS

| | | |
|---|---|---|
| 191292 | 8/1986 | European Pat. Off. . |
| 317272 | 11/1988 | European Pat. Off. . |
| 57-120514 | 7/1982 | Japan . |
| 62-22710 | 1/1987 | Japan . |
| 62-4212 | 1/1987 | Japan . |

*Primary Examiner*—C. Warren Ivy
*Assistant Examiner*—Evelyn Huang
*Attorney, Agent, or Firm*—John M. Howell; Daniel F. Nesbitt; Jacobus C. Rasser

[57] ABSTRACT

The present invention provides a useful cosmetic having high ultraviolet-screening effects (sunscreening effects), and excellent safety, and giving a natural makeup finish. This composition comprises a metal oxide flake having an average thickness of from 0.01 to 3 μm, and an average size of from 1 to 100 μm, and a ultraviolet absorbent-encapsulated polymer resin particle obtained by polymerization of a polymer resin monomer uniformly mixed with an ultraviolet absorbent.

14 Claims, 2 Drawing Sheets

COSMETICS HAVING SUNSCREEN PROPERTIES

This is a continuation-in-part of application Ser. No. 07/849,923, filed on Mar. 12, 1992, abandoned Mar. 30, 1994.

TECHNICAL FIELD

This invention relates to sunscreening cosmetics, and more particularly to cosmetics comprising a combination of a metal oxide flake and an ultraviolet absorbent-encapsulated polymer resin particle so as to exhibit high sunscreening effects.

BACKGROUND OF THE INVENTION

Ultraviolet rays reaching the ground are known to include middle ultraviolet rays (290–320 µm; called UV-B) which induce rash of the skin, followed by inflammation leading to skin darkening and are regarded as one of causes of cutaneous cancer, and near ultraviolet rays (320–400 nm; called UV-A) which are less causative of rash but oxidize reduced melanin in the skin to cause deposition of melanin pigment leading to skin darkening or which are regarded to accelerate aging of the skin through long-term exposure.

With elucidation of the influences of ultraviolet rays on the skin, there has been an increasing demand for sunscreening cosmetics. A sun protection factor (SPF) value has been proposed as an index for protection of the skin from ultraviolet rays, and a higher SPF value is deemed to indicate a higher sunscreening effect. Reference can be made, for example, to Fukuda Minoru, *KOSHOKAISHI*, "Sun-Screen and SPF," Vol. 8, No. 4, pp. 315–323 (1984).

In general, sunscreening cosmetics contain ultraviolet absorbents or ultraviolet scattering agents for obtaining high SPF values.

Known ultraviolet absorbents include benzophenone compounds, cinnamic acid compounds, and benzoic acid compounds. Achievement of effective sunscreening requires incorporating a relatively large quantity of the ultraviolet absorbent into cosmetic compositions. However, incorporating a large quantity of the ultraviolet absorbent causes various problems, such as reduction in compatibility with cosmetic bases, adverse influences on cosmetic bases (e.g., denaturation), decomposition of the ultraviolet absorbent which leads to reduction in ultraviolet absorptivity, coloring, etc., and impairment of safety (e.g., increased irritation to the skin). Therefore, use of ultraviolet absorbents as cosmetic material involves many disadvantages, and cosmetics containing such materials in large quantities lose their values as cosmetics.

On the other hand, ultraviolet screening agents include zinc oxide, titanium oxide, zirconium oxide, and kaolin. These inorganic pigments show an effect of screening a broad range of ultraviolet rays, are less liable to denaturation on exposure to ultraviolet rays, and are less irritating to the skin because they do not penetrate into the skin. However, when they are applied to the skin, they give an unnatural white look to the skin due to their high covering power.

In order to overcome these disadvantages, zinc oxide, titanium oxide, zirconium oxide, etc. in the form of fine particles have been proposed. However, such particles undergo secondary agglomeration when incorporated into cosmetics, not only failing to exhibit sufficient sunscreening effects as expected from sunscreening cosmetics, but also resulting in poor spreadability on the skin.

In the light of the above-described circumstances, plate-like metal oxides have been proposed for use as cosmetic materials. These materials are said to have high safety, provide a satisfactory makeup finish, and exhibit high ultraviolet screening ability, as disclosed in Japanese Patent Application Laid-Open Nos. Sho-61-161212, Sho-62-4212, Sho-63-166819, and Hei-1-175921.

Although these materials are safe and give a natural makeup finish, the sunscreening effects attained are still insufficient irrespective of whether they are used alone or in combination with ordinary ultraviolet absorbents in amounts that cause no safety problem.

Accordingly, there still has been a demand in the art to develop cosmetics that are safe to use and yet have high sunscreening effects.

An object of the present invention, therefore, is to solve the above-mentioned problems. That is, an object of the present invention is to provide a cosmetic which exhibits high ultraviolet-screening effects (sunscreening effects), which is excellent in safety, which stably maintains an ultraviolet absorbent in the base thereof, and which gives a natural makeup finish.

SUMMARY OF THE INVENTION

The present invention relates to sunscreening cosmetic compositions for application to the skin, comprising:

(a) an effective amount (preferably from about 1% to about 70%) of metal oxide flakes (preferably zinc oxide, titanium oxide, zirconium oxide and mixtures thereof) having a thickness of from about 0.01 to about 3 µm and an average size of from about 1 to about 100 µm, and (b) an effective amount (preferably from about 0.1% to about 70%) of a ultraviolet absorbent-encapsulated polymer resin particle obtained by polymerizing a monomer of the polymer resin uniformly mixed with the UV absorbent.

In preferred polymer resin particles, the polymer resin membrane encapsulates a core comprising the ultraviolet absorbent. Preferred polymer resin materials include vinyl polymers, olefin-vinyl polymers, olefin-alkyl polymers, polyamides, acrylic resins, polystyrene, polyesters, and mixtures thereof; while preferred ultraviolet absorbents include aminobenzoic acid and its derivatives, salicylic acid and its derivatives, cinnamic acid and its derivatives, benzophenone derivatives, urocanic acid and its derivatives, and mixtures thereof.

DETAILED DESCRIPTION OF THE INVENTION

The inventors have conducted extensive investigations to solve the above-described problems, and as a result, found that a cosmetic containing a metal oxide flake having an average thickness of from 0.01 to 3 µm and an average size of from 1 to 100 μm and a polymer resin particle encapsulating therein an ultraviolet absorbent which is obtained by polymerization of a monomer for a polymer resin uniformly mixed with an ultraviolet absorbent exhibits ultraviolet-screening effects (sunscreening effects), has excellent safety, stably maintains an ultraviolet absorbent in the base thereof, and gives a natural makeup finish, thus having completed the present invention.

That is, when a metal oxide flake and an ultraviolet absorbent-encapsulated polymer resin particle are combined, a significantly high SPF value can be obtained even if the total amount of these two components in cosmetics is relatively small. From the standpoint of safety, there is no need to consider the safety problem since the above-mentioned synergistic effect of the two components allow the requisite amount of the ultraviolet absorbent to be relatively reduced and, in addition, the ultraviolet absorbent is encapsulated within the polymer resin, and thus not brought into direct contact with the skin. Moreover, from the standpoint of utility, the cosmetics using these two components exhibit excellent performance, for example, in terms of makeup finish and spreadability on the skin.

The plate-like metal oxide which can be used in the present invention has an average thickness of from 0.01 to 3 μm and an average size of from 1 to 100 μm. The term "average thickness" as used herein means the average of thickness values measured on 100 flakes, and the term "average size" as used herein means the average value of (maximum diameter+minimum diameter)/2 as measured on 100 flakes. The metal oxide is not limited in kind as long as it is acceptable as a cosmetic material and has a shape or size within the above-specified range. Useful metal oxides include, for example, inorganic pigments, e.g., zinc oxide, titanium oxide, and zirconium oxide.

The metal oxide flakes which can be used in the present invention may be prepared, for example, as follows. First of all, a plate-like metal oxide of a desired thickness is prepared, for example, using a method in which an organic solvent solution of metal oxide is coated on a smooth surface and the resulting film is cracked by the action of steam to obtain thin plates as described in U.S. Pat. No. 2,941,895; a method in which a metal oxide solution is coated on a gelatin film, and the gelatin film is then dissolved as described in Japanese Patent Publication No. Sho-30-473; a method of using vacuum evaporation as described in Japanese Patent Publication No. Sho-39-25280; or a method in which metal oxide fibers are treated with an acid and then with heat as described in Japanese Patent Application Laid-Open No. Sho-58-88121. Subsequently, the resulting plate-like metal oxide is ground in a dry ball mill, a wet ball mill, a vibration mill, a jet mill, etc. or subjected to one or more of classification means, such as vibrating sieves (e.g., a gyroshifier, a hammer screen), wet classifiers (e.g., a spiral classifier, a hydraulic classifier), dry classifiers (e.g., dynamic or centrifugal air classifier), or flotation, to obtain a specific size. Thin layered titanium oxide falling within the scope of the present invention is available from Sumitomo Chemical Co., Ltd. under the trade name of Luxelen (registered trademark).

The polymer resin encapsulating therein an ultraviolet absorbent has such a structure wherein a polymer resin membrane encapsulates a core comprising an ultraviolet absorbent. The ultraviolet absorbent-encapsulated polymer resin particle of the present invention having such a structure is different from a mere mixture of a resin powder and an ultraviolet absorbent as disclosed in Japanese Patent Application Laid-Open No. Sho-62-22710. Namely, the resin material of the latter resin powder has a slow release property so that the ultraviolet absorbent is released into the cosmetic base over time causing the problem of poor stability of resin, whereas the ultraviolet absorbent-encapsulated polymer resin particle used in the present invention is free from this disadvantage.

The polymer resin particle materials capable of encapsulating ultraviolet absorbents include, while not being limited to, vinyl polymers, olefin-vinyl polymers, olefin-allyl polymers, polyamides, acrylic resins, polystyrene, and polyesters.

The ultraviolet absorbents which can be encapsulated in the polymer resin materials include, while not being limited to, aminobenzoic acid and/or derivatives thereof, salicylic acid and/or derivatives thereof, cinnamic acid and/or derivatives thereof, benzophenone derivatives, and urocanic acid and/or derivatives thereof. Specific examples of these ultraviolet absorbents are 2-hydroxy-4-methoxybezophenone, 2-hydroxy-4-methoxybenzophenone-5-sulfonic acid, 2,2'-dihydroxy-4-methoxybenzophenone, diethanolamine p-methoxyhydrocinnamate, ethyl-dihydroxypropyl p-amino-benzoate, glyceryl p-aminobenzoate, homomethyl salicylate, methyl o-amine-benzoate, 2-ethylhexyl-2-cyano-3,3-diphenyl-acrylate, octyldimethyl p-aminobenzoate, 2-ethylhexyl-p-methoxycinnamic acid, 2-ethylhexylsalicylic acid, p-amino-benzoic acid, 2-phenylbenzimidazoyl-5-sulfonic acid, triethanolamine salicylate, 3-(4-methylbenzylidene)-camphor, 2,4-dihydroxybenzophenone, 2,2'4,4'-tetrahydroxybenzophenone, 2,2'-dihydroxy-4,4'-dimethoxybenzophenone, octabenzone, 4-isopropyldibenzoylmethane, 4-t-butyl-4'-methoxybenzoyl-methane, 2-ethyl-2-cyano-3,3'-diphenylacrylate, urocanic acid, and ethyl urocanate. These ultraviolet absorbents may be used either individually or as a mixture of two or more thereof. They may be used in combination with conventional additives which can be used in cosmetics, such as fats and oils, esters, hydrocarbons, and liquid higher alcohols.

The ultraviolet absorbent-encapsulated polymer resin particle of the present invention can be made by in-situ polymerization method. In the in-situ polymerization, the polymerizing reaction is conducted for a mixture of the monomer(s) and ingredients to be encapsulated therein. In the present invention, the ultraviolet absorbent and, if desired, other optional components such as fats and oils are mixed with the monomer of the polymer resin, and emulsified in water to make an oil-in-water emulsion, and then polymerized to obtain the microcapsule-like particles. Such particles have a particle size of about 1–100 μm. It is believed that, particles of this size can encompass ingredients such as oils and fats, as well as easily collapse upon use. It is further believed that, when comprised in face powders, emulsified foundations, and cosmetic creams, these microcapsules can prevent the encapsulated ingredients from interacting with other components in the composition, thereby stabilizing the encapsulated ingredients. It is also believed that, after collapsing, the membrane of the capsules themselves become thin layers and spread on the skin. These layers are transparent, and thus invisible on the skin.

The amount of the ultraviolet absorbent to be encapsulated in the polymer resin particle is usually not less than about 0.01% by weight, and preferably of from about 1.0 to about 50% by weight, per 100% by weight of the particle, depending on factors such as the amount of ultraviolet absorbent and polymer resin to be incorporated into cosmetics, the kind of the ultraviolet absorbent used, and the desired sunscreening effects. If the amount of the ultraviolet absorbent in the resin is so small as less than about 0.01% by weight, the ultraviolet absorbent-encapsulated resin particle tends to fail to produce sufficient sunscreening effects even when incorporated into cosmetics in a high level. On the other hand, when the ultraviolet absorbent exceeds about 50% by weight of the particle, the polymer resin membrane encapsulating the ultraviolet absorbent becomes thin and unstable with time so that the membrane is apt to break when incorporated into cosmetics.

The preferred ultraviolet absorbent-encapsulated polymer resin particle has a size of from about 5 to about 20 μm.

The amount of metal oxide flake to be incorporated into cosmetics usually ranges from about 1 to about 70% by weight based on the total weight of a cosmetics though varying depending on the desired degree of sunscreening effects, the amount of the ultraviolet absorbent-encapsulated polymer resin particle to be used, and the like. If it is less than about 1% by weight, sufficient sunscreening effects will not be exhibited. If it exceeds about 70% by weight, the resulting cosmetics cannot be uniformly applied to the skin or they show poor utility (spreadability, durability, color formation, etc.) and are thus unsatisfactory as sunscreening cosmetics.

The amount of ultraviolet absorbent-encapsulated polymer resin particle to be incorporated into a cosmetic usually ranges from about 0.1 to about 70% by weight based on the total weight of the cosmetic, depending on factors such as the desired degree of sunscreening effects, and the amount of the metal oxide flake used in combination. If it is less than about 0.1% by weight, sufficient sunscreening effects cannot be obtained. If it exceeds about 70% by weight, the resulting cosmetics cannot be uniformly applied to the skin or they show poor utility (spreadability, durability, color formation, etc.) and are thus unsatisfactory as sunscreening cosmetics.

In addition to the metal oxide flake and the ultraviolet absorbent-encapsulated polymer resin particle, the cosmetic compositions of the present invention may further contain, a cosmetically acceptable topical carrier which may include conventional levels of additives commonly employed in cosmetics, such as surface active agents, oily components, moisture retaining agents, pigments, preservatives, etc. See, for example, U.S. Pat. No. 5,041,282, Sabatelli et al, Aug. 20, 1991, incorporated hereby by level of these components will vary based upon the form which the final cosmetic composition will have (e.g. a lotion, a foundation, a face powder, a lipstick, a cream or mousse, to name a few). This cosmetically acceptable carder comprises the balance of the composition and would generally be present at up to about 98.9%, preferably from about 20% to about 98.9%, of the composition.

Without being bound by theory, it is believed that the unexpectedly enhanced ultraviolet-screening effects provided by the present invention result from the fact that the ultraviolet absorbent-encapsulated polymer resin particle is uniformly dispersed among layers of metal oxide flakes to absorb ultraviolet rays which remain unabsorbed by the metal oxide flakes alone.

EXAMPLES

The present invention is now illustrated in greater detail by way of Examples, but it should be understood that the present invention is not deemed to be limited thereto. All percentages, ratios, and parts are based on weight unless otherwise specified.

1. Preparation
(1) Metal Oxide Flakes
"Luxelen" (registered trademark) produced by Sumitomo Chemical Co., Ltd. was used as titanium oxide. Luxelen has an average thickness of 0.2 μm, an average size of 3 to 20 μm, a refractive index of 2.7, and a reflectance of 7 to 15%.

Zinc oxide and zirconium oxide used in Examples had an average thickness and average size falling within the ranges as specified in the present invention.

(2) Ultraviolet Absorbent-Encapsulated Polymer Resin Particle

Polymethyl methacrylate resin (PMMA) particles encapsulated with octyldimethyl p-aminobenzoate [UV-(1)] and/or 4-t-butyl-4'-methoxybenzoylmethane[UV-(2)] as an ultraviolet absorbent in the proportions shown in Table 1 below were used.

TABLE 1

| UV-Absorbent encapsulated in PMMA Particles | | |
|---|---|---|
| Designation | Proportion of UV-(1) | Proportion of UV-(2) |
| UV-Powder 0000 | 0(%) | 0(%) |
| UV-Powder 0703 | 7(%) | 3(%) |
| UV-Powder 1010 | 10(%) | 10(%) |
| UV-Powder 2000 | 20(%) | 0(%) |

UV-Powder 0000 can be suitably made as follows: 495 parts of Methylmethacrylate, 20 pads Methacrylic Acid and 15 pads Diisopropyl Peroxydicarbonate are mixed to make an oil phase. Next, 6300 pads of Deionized water, 1390 parts of Colloidal Silica Emulsion having 20% solid component, 90 parts of 10% solution of condensate of Diethanolamine and Adipic Acid, and an amount of Hydrochloric Acid enough to make the solution have a pH of 3.5 is combined to make a water phase. The obtained oil phase and water phase is stirred at a rate of 10,000 rpm for 60 seconds, so that the oil phase is emulsified in the water phase. The emulsion is placed in a condensation reactor whose content had been replaced with nitrogen, and is allowed to react for 20 hours under stirring at 30 rpm at 55°–60° C. The product thus obtained is purified by centrifugation and washing with water repeatedly. Finally, a cake-type product having 32% water content and 19μ average particle size is obtained. This cake-type product is dried by a flash drying procedure, and a soft spherical microcapsule like particle which can be collapsed upon pressure having a water content of 0.8% is obtained.

UV-Powder 0703 can be suitably made as follows: 495 parts of Methylmethacrylate, 20 parts Methacrylic Acid, 250 parts octyldimethyl p-aminobenzoate, 110 pads 4-tert-Butyl-4'-Methoxy-Dibenzoylmethane and 15 pads Diisopropyl Peroxydicarbonate are mixed to make an oil phase. Next 6300 parts of Deionized Water, 1390 parts of Colloidal Silica Emulsion having 20% solid component, 90 parts of 10% solution of condensate of Diethanolamine and Adipic Acid; and an amount of Hydrochloric Acid enough to make the solution have a pH of 3.5 is combined to make a water phase. The obtained oil phase and water phase is emulsified, reacted, and purified as described for UV-Powder 0000 to obtain a cake-type product having 32% water content and 10μ average particle size. This cake-type product is dried by a flash drying procedure, and a soft spherical microcapsule like particle which can be collapsed upon pressure having a water content of 0.8% is obtained.

UV-Powder 1010 can be suitably made as follows: 495 parts of Methylmethacrylate, 20 parts Methacrylic Acid, 350 parts octyldimethyl p-aminobenzoate, 350 parts 4-tert-Butyl-4'-Methoxy-Dibenzoylmethane and 15 parts Diisopropyl Peroxydicarbonate are mixed to make an oil phase. Next 6300 parts of Deionized Water, 1390 parts of Colloidal Silica Emulsion having 20% solid component, 90 parts of 10% solution of condensate of Diethanolamine and Adipic Acid, and an amount of Hydrochloric Acid enough to make the solution have a pH of 3.5 is combined to make a water phase. The obtained oil phase and water phase is emulsified, reacted, and purified as described for UV-Powder 0000 to obtain a cake-type product having 32% water content and 12μ average particle size. This cake-type product is dried by a flash drying procedure, and a soft spherical microcapsule like particle which can be collapsed upon pressure having a water content of 0.8% is obtained.

UV-Powder 2000 can be suitably as follows: 495 parts of Methylmethacrylate, 20 parts Methacrylic Acid, 700 parts octyldimethyl p-aminobenzoate, and 15 parts Diisopropyl Peroxydicarbonate are mixed to make an oil phase. Next, 6300 parts of Deionized Water, 1390 parts of Colloidal Silica Emulsion having 20% solid component, 90 parts of 10% solution of condensate of Diethanolamine and Adipic Acid, and an amount of Hydrochloric Acid enough to make the solution have a pH of 3.5 is combined to make a water phase. The obtained oil phase and water phase is emulsified, reacted, and purified as described for UV-Powder 0000 to obtain a cake-type product having 32% water content and 10μ average particle size. This cake-type product is dried by a flash drying procedure, and a soft spherical microcapsule like particle which can be collapsed upon pressure having a water content of 0.8% is obtained.

2. Experimentation (1) Ultraviolet Absorption

Figure 1:
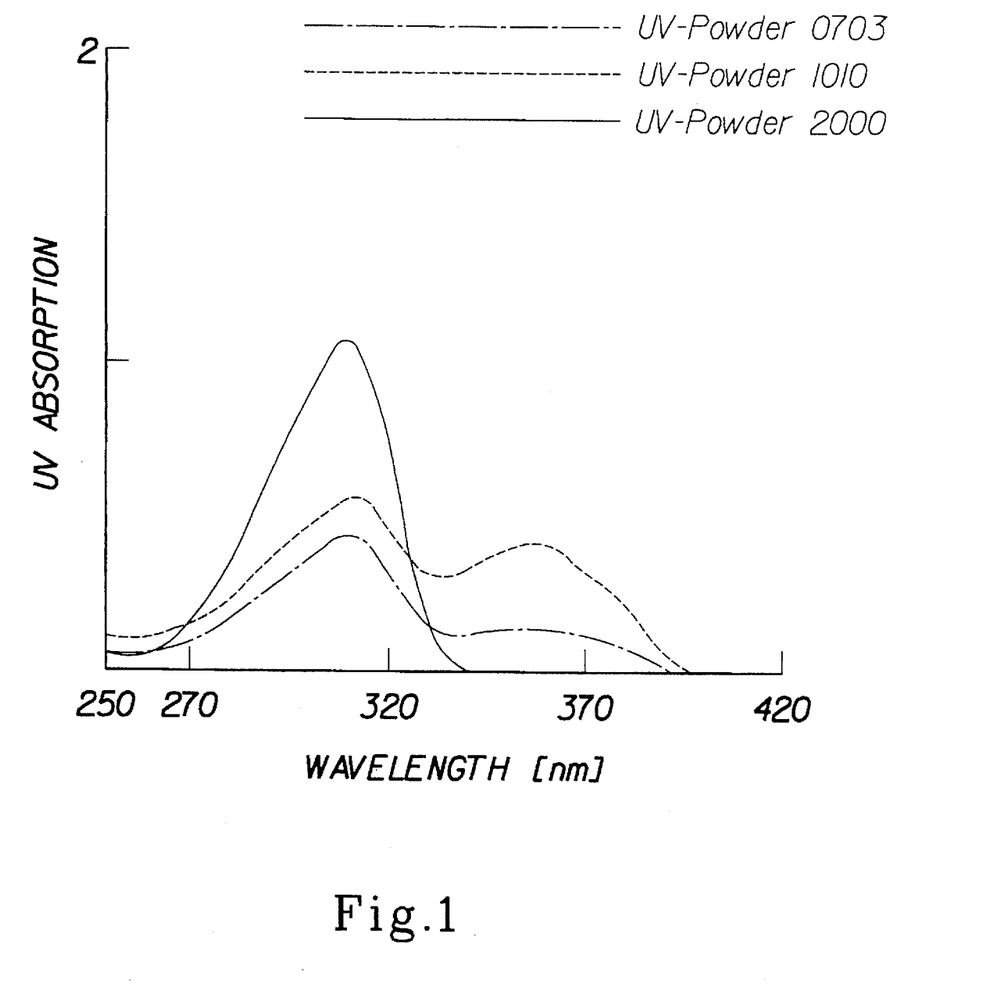
FIG. 1 shows characteristic ultraviolet absorption curves of the ultraviolet absorbent-encapsulated polymer resin particles of the present invention and polymer resin particles which do not contain ultraviolet absorbents.

2% of each of the UV-Powders as shown in Table 1 thus obtained was uniformly dispersed in liquid paraffin as a dispersion medium to prepare a paste. Characteristic ultraviolet absorption curves of each paste (thickness: 7 μm) are shown in FIG. 1. UV-Powder 0000 showed no ultraviolet absorption characteristics, revealing its absorption spectrum as a base line.

(2) SPF Value

Ten or more Hartley female guinea pigs (b.w.:250–350 g) were used as test animals. The back of the animal was shaved with an electric shaver, and any remaining hair was removed with a depilatory cream prior to exposure to sunlight. The animal being fixed in braces, the shaved back was divided into a right part and a left part along the back bone. One of the parts (right or left) was uniformly coated with a sample to give a spread of 2 mg/cm, with the other part (left or right) remaining uncoated. Then, a 2×10 cm sunscreening tape having seven vertically aligned 1×1 cm square openings was adhered to each of the coated part and the uncoated part. Sunlight irradiation was started 15 minutes after the coating. While monitoring the UV-irradiation dose by means of a UV integrating meter, Radiometer, manufactured by Suga Test Instrument Co., Ltd., the openings were successively shut against sunlight with sunscreening tape at a point when a respective predetermined UV-irradiation dose, varying stepwise, was reached. On shutting all the openings, UV-irradiation was ceased, the tape was stripped off, and the animal was allowed to stand for 24 hours before evaluation.

The skin reaction in the area corresponding to each opening was observed. The integrated irradiation dose on the area which showed the weakest erythema (rash) was taken as a minimum erythema dose (MED).

An SPF value for each sample under test was calculated from equation:

$$SPF = \frac{MED \text{ on Coated Part}}{MED \text{ on Non-Coated Part}}$$

In the following Examples, the SPF values of Examples 2 and 9 and Comparative Examples 1, 4, 6 and 9 were measured as described herein. The SPF values for the other Examples and Comparative Examples were estimated based on measured values of similar compositions.

(3) Utility (Sensory Test)

Sensory tests were conducted with respect to a makeup finish and spreadability on the skin. Fifteen to twenty female panel members were asked to make up with each sample in the usual manner and to evaluate the finish and spreadability according to a 5-rank system: 5 ... excellent; 4 ... good; 3 ... moderate; 2 ... slightly bad; 1 ... bad. The sum of scores of each sample gained was divided by the number of panel members, and the quotient was judged as follows.

| Point: | 5–4.5 | 4.5–3.5 | 3.5–2.5 | 2.5 or less |
|---|---|---|---|---|
| Judgment: | ⊚ | ○ | △ | X |

3. Cosmetic Compositions and Results

Examples 1–7 and Comparative Examples 1–14 shown in Table 2 can be prepared by any conventional method well known in the art. A suitable method is as follows:

All powdery components (components except liquid paraffin, perfume and preservative are mixed and pulverized with a hammer type pulverizer. The remaining components which make the binder base are uniformly dissolved by stirring. The binder base is sprayed onto the powdery components, and the obtained mixture is further pulverized. The obtained composition is placed into a mold and pressed into a cake.

The obtained pressed face powders were used to determine SPF value and sensory performance as described in the experimental part above. The obtained results are also shown in Table 2.

As can be seen from Table 2, the cosmetics according to the present invention in which titanium oxide flakes and the ultraviolet absorbent-encapsulated polymer resin particles (UV Powders 0703, 1010, 2000) are used in combination (Examples Nos. 1 to 7) are excellent in both SPF value and utility, especially showing high SPF values, as compared with those containing titanium oxide alone (Comparative Examples 1–5 and Comparative Example 7 in which UV Powder 0000, a polymer resin particle encapsulating no ultraviolet absorbent was used in combination), those containing titanium oxide flakes alone (Comparative Example Nos. 6 and 11), those containing the ultraviolet absorbent-encapsulated polymer particle alone (Comparative Example Nos. 8–10), those containing titanium oxide in combination with the ultraviolet absorbent (octyldimethyl p-aminobenzoate) (Comparative Example No. 12), and those containing titanium oxide in combination with titanium oxide flakes.

TABLE 2

Formulation of Compressed Face Powder and Test Results

| Raw Material | Compar. Example 1 | Compar. Example 2 | Compar. Example 3 | Compar. Example 4 | Compar. Example 5 | Compar. Example 6 | Compar. Example 7 | Compar. Example 8 | Compar. Example 9 | Compar. Example 10 |
|---|---|---|---|---|---|---|---|---|---|---|
| Titanium oxide | 10.0 | 20.0 | 10.0 | 10.0 | 10.0 | 10.0 | 10.0 | 10.0 | 10.0 | 10.0 |
| Mica | 30.0 | 30.0 | 30.0 | 30.0 | 30.0 | 30.0 | 30.0 | 30.0 | 30.0 | 30.0 |
| Talc | 35.0 | 25.0 | 25.0 | 25.0 | 25.0 | 25.0 | 25.0 | 25.0 | 25.0 | 25.0 |
| Sericite | 10.0 | 10.0 | 10.0 | 10.0 | 10.0 | 10.0 | 10.0 | 10.0 | 10.0 | 10.0 |
| Coloring pigment | 5.0 | 5.0 | 5.0 | 5.0 | 5.0 | 5.0 | 5.0 | 5.0 | 5.0 | 5.0 |
| Zinc Oxide | | | 10.0 | | | | | | | |
| Titanium oxide fine particles | | | | 10.0 | | | | | | |
| Zinc oxide fine particles | | | | | 10.0 | | | | | |
| Titanium oxide flakes (Luxelen) | | | | | | 10.0 | | | | |
| UV-Powder 0000 | | | | | | | 10.0 | | | |
| UV-Powder 0703 | | | | | | | | 10.0 | | |
| UV-Powder 1010 | | | | | | | | | 10.0 | |
| Octyldimethyl p-aminobenzoate | | | | | | | | | | 10.0 |
| Liquid paraffin | 10.0 | 10.0 | 10.0 | 10.0 | 10.0 | 10.0 | 10.0 | 10.0 | 10.0 | 10.0 |
| Perfume | adequate amount | adequate amount | adequate amount | adequate amount | adequate amount | adequate amount | adequate amount | adequate amount | adequate amount | adequate amount |
| Preservative | adequate amount | adequate amount | adequate amount | adequate amount | adequate amount | adequate amount | adequate amount | adequate amount | adequate amount | adequate amount |
| SPF value | 6.9 | 9.1 | 8.2 | 7.8 | 8.1 | 9.3 | 6.7 | 8.0 | 8.4 | 8.8 |
| Makeup finish | ○ | x | ○ | ○ | ○ | ⊙ | ⊙ | ⊙ | ⊙ | ⊙ |
| Spreadability | ○ | x | Δ | Δ | Δ | ○ | ⊙ | ⊙ | ⊙ | ⊙ |

| Raw Material | Compar. Example 11 | Compar. Example 12 | Example 1 | Example 2 | Example 3 | Compar. Example 13 | Example 4 | Example 5 | Compar. Example 14 | Example 6 | Example 7 |
|---|---|---|---|---|---|---|---|---|---|---|---|
| Titanium oxide | 10.0 | 10.0 | 10.0 | 10.0 | 10.0 | 10.0 | 10.0 | 10.0 | 10.0 | 10.0 | 10.0 |
| Mica | 30.0 | 30.0 | 30.0 | 30.0 | 30.0 | 30.0 | 30.0 | 30.0 | 30.0 | 30.0 | 30.0 |
| Talc | 20.0 | 25.0 | 20.0 | 20.0 | 20.0 | 5.0 | 4.0 | 18.0 | 15.0 | 13.0 | 13.0 |
| Sericite | 10.0 | 10.0 | 10.0 | 10.0 | 10.0 | 10.0 | 10.0 | 10.0 | 10.0 | 10.0 | 10.0 |
| Coloring pigment | 5.0 | 5.0 | 5.0 | 5.0 | 5.0 | 5.0 | 5.0 | 5.0 | 5.0 | 5.0 | 5.0 |
| Zinc Oxide | | | | | | | | | | | |
| Titanium oxide fine particles | | | | | | | | | 10.0 | | |
| Zinc oxide fine particles | | | | | | | | | | | |
| Titanium oxide flakes (Luxelen) | 10.0 | | 10.0 | 10.0 | 10.0 | 30.0 | 30.0 | 2.0 | 10.0 | 10.0 | 10.0 |
| UV-Powder 0000 | 5.0 | | | | | | | | | | |
| UV-Powder 0703 | | 5.0 | | | | | | | | | 2.0 |
| UV-Powder 1010 | | | | 5.0 | | | | | | | |
| UV-Powder 2000 | | | | | 5.0 | | 1.0 | 15.0 | | 2.0 | |
| Octyldimethyl p-aminobenzoate | | 2.0 | | | | | | | | | |
| Liquid paraffin | 10.0 | 8.0 | 10.0 | 10.0 | 10.0 | 10.0 | 10.0 | 10.0 | 10.0 | 10.0 | 10.0 |
| Perfume | adequate amount | adequate amount | adequate amount | adequate amount | adequate amount | adequate amount | adequate amount | adequate amount | adequate amount | adequate amount | adequate amount |
| Preservative | adequate amount | adequate amount | adequate amount | adequate amount | adequate amount | adequate amount | adequate amount | adequate amount | adequate amount | adequate amount | adequate amount |
| SPF value | 7.1 | 7.5 | 15.2 | 16.3 | 17.6 | 9.4 | 15.8 | 14.9 | 9.2 | 16.6 | 15.8 |
| Makeup finish | ⊙ | ⊙ | ⊙ | ⊙ | ⊙ | ○ | ○ | ⊙ | ⊙ | ⊙ | ⊙ |
| Spreadability | ⊙ | ⊙ | ⊙ | ⊙ | ⊙ | Δ | ○ | ⊙ | ○ | ⊙ | ⊙ |

Table 3 below shows formulations of multi-layer cosmetics their SPF values and utility thereof. These multi-layer cosmetics comprise 2 or 3 separate layers in a stationary state, and are homogeneously dispersed by shaking before use.

TABLE 3

Formulation of Multi-Layer Cosmetics and Test Results

| COMPONENTS | | Example 8 (%) | Comparative Example 15 (%) |
|---|---|---|---|
| Phase A | Octyl isopelargonate | 3.00 | 3.00 |
| | (POE 40) Tetraoleyl sorbitol | 0.05 | 0.05 |
| | Octyldimethyl p-amino-benzoate | 0.50 | 0.50 |
| | 4-t-Butyl-4'-methoxy-benzoylmethane | 0.50 | 0.50 |
| Phase B | Purified Water | 72.95 | 78.95 |
| | 1,3-Butylene glycol | 3.00 | 3.00 |
| | Ethanol | 14.00 | 14.00 |
| Phase C | Zirconium oxide flakes | 5.00 | |
| | UV-Powder 1010 | 1.00 | |
| Results | SPF value | 16.3 | 6.2 |
| | Natural makeup finish | ⊚ | ⊚ |
| | Utility (moist to feel, though dry to touch) | ⊚ | △ |

The compositions shown in Table 3 can be prepared by any conventional method well known in the art. A suitable method is as follows:

Components of Phase A are uniformly dissolved by stirring. Components of Phase B are uniformly dissolved by stirring. Phase A is poured into Phase B under stirring. Finally, Phase C is poured into the obtained mixture (Phase A +B) under stirring and further mixed until the composition becomes uniform.

Figure 2:
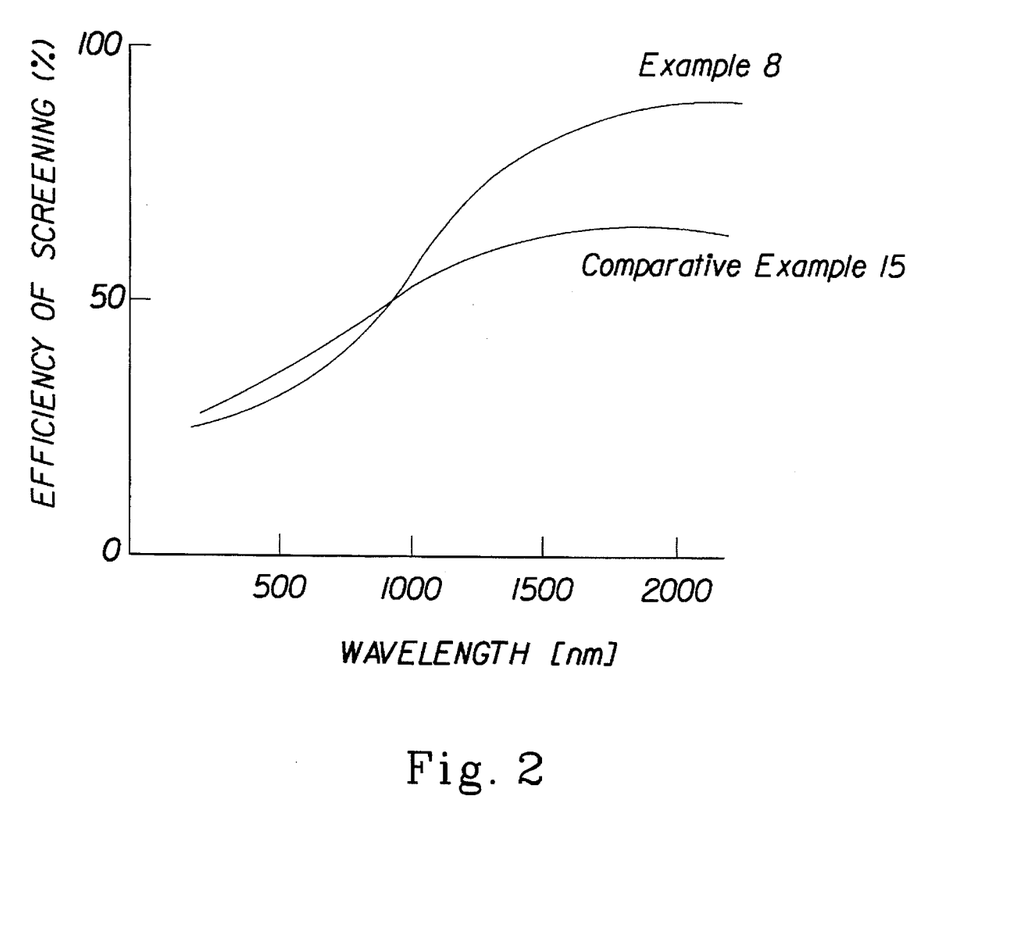
FIG. 2 shows infrared-screening effects of the multi-layer cosmetics, Example 8 and Comparative Example 15.

The cosmetic of Exmaple 8 according to the present invention is significantly superior to that of Comparative Example 15 in SPF value and also excellent in utility, providing high sunscreening effects. Further, the cosmetic of Example 8 also provided excellent infra-red-screening effect as shown in FIG. 2.

Various cosmetics falling within the scope of the present invention were prepared as follows and evaluated for SPF value and utility.

EXAMPLE 9

Sunscreening Cream

| COMPONENTS | | AMOUNT (%) |
|---|---|---|
| Phase A | Stearic Acid | 4.0 |
| | Self-emulsifiable glycerin monostearate | 3.0 |
| | Cetanol | 2.0 |
| | Bleached bees wax | 3.0 |
| | Olive Oil | 5.0 |
| | Squalane | 10.0 |
| | Antioxidant | adequate amount |
| Phase B | Triethanolamine | 2.0 |
| | Propylene glycol | 7.0 |
| | Bentonite | 0.5 |
| | Preservative | adequate amount |
| | Titanium oxide flakes (Luxelen) | 10.0 |
| | UV-Powder 0703 | 1.0 |
| | Perfume | adequate amount |
| | Purified Water | qs 100.0 |

Examples 9 shown above can be prepared by any conventional method well known in the art. A suitable method is as follows:

Components of Phase A are homogeneously melted at 80°–85 °C. Separately, components of Phase B except for perfume are homogeneously melted at 80°–85° C. Melted Phase A is added to melted Phase B under mixing. The obtained mixture is passed through a colloid mill until it becomes uniform. Finally perfume is added, and the composition is cooled to room temperature.

The sunscreening cream having the above formulation had an SPF value of 17.2 and exhibited satisfactory spreadability on the skin to give a natural makeup finish.

EXAMPLE 10

Sunscreening Milky Lotion

| COMPONENTS | | AMOUNT (%) |
|---|---|---|
| Phase A | (POE 20) Oleyl ether | 1.2 |
| | Sorbitan sesquioleate | 0.8 |
| | Bleached bees wax | 0.5 |
| | Vaseline | 2.0 |
| | Squalane | 5.0 |
| Phase B | Propylene glycol | 5.0 |
| | Ethanol | 3.0 |
| | Preservative | adequate amount |
| | Xanthan gum | 0.2 |
| | Zinc oxide flakes | 7.0 |
| | UV-Powder 2000 | 3.0 |
| | Perfume | adequate amount |
| | Purified Water | qs 100.0 |

Example 10 shown above can be prepared by any conventional method well known in the art, for example, the method described for Example 9.

The sunscreening milky lotion having the above formulation had an SPF value of 16.7 and exhibited satisfactory spreadability on the skin to give a natural makeup finish.

EXAMPLE 11

Foundation (O/W Type)

| COMPONENTS | | AMOUNT (%) |
|---|---|---|
| Phase A | Stearic Acid | 4.0 |
| | Glycerin monostearate | 2.0 |
| | Cetostearyl alcohol | 1.5 |
| | Isopropyl myristate | 7.0 |
| | Liquid paraffin | 10.0 |
| | Silicone oil | 5.0 |
| Phase B | Triethanolamine | 1.5 |
| | Glycerin | 4.0 |
| | Bentonite | 1.0 |
| | Preservative | adequate amount |
| | Titanium oxide | 8.0 |
| | Kaolin | 3.0 |
| | Talc | 3.0 |
| | Titanium oxide flakes | 5.0 |
| | UV-Powder 1010 | 1.0 |
| | Coloring pigment | 2.0 |
| | Perfume | adequate amount |
| | Purified Water | qs 100.0 |

Example 11 shown above can be prepared by any conventional method well known in the art, for example, the method described for Example 9.

The creamy foundation having the above formulation had an SPF value of 16.2 and exhibited satisfactory spreadability on the skin to give a natural makeup finish.

EXAMPLE 12

Foundation (O/W Type)

| COMPONENTS | | AMOUNT (%) |
|---|---|---|
| Phase A | Sorbitan sesquioleate | 3.0 |
| | Self-emulsifiable glycerin monostearate | 2.0 |
| | Aluminum stearate | 0.5 |
| | Cerasine wax | 5.0 |
| | Squalane | 10.0 |
| | Sesame oil | 15.0 |
| | Vaseline | 5.0 |
| | Ethyl urocanate | 2.0 |
| Phase B | Propylene glycol | 5.0 |
| | Preservative | adequate amount |
| | Magnesium oxide | 0.5 |
| | Titanium oxide | 4.0 |
| | Zirconium oxide | 4.0 |
| | Talc | 4.0 |
| | Titanium oxide flakes | 6.0 |
| | UV-Powder 0703 | 2.0 |
| | Perfume | adequate amount |
| | Purified Water | qs 100.0 |

Example 12 shown above can be prepared by any conventional method well known in the art, for example, the method described for Example 9.

The creamy foundation having the above formulation had an SPF value of 18.7 and exhibited satisfactory spreadability on the skin to give a natural makeup finish and was excellent in durability after makeup.

EXAMPLE 13

Clear Lotion

| COMPONENTS | | AMOUNT (%) |
|---|---|---|
| Phase A | Ethanol | 10.0 |
| | (POE 20) Sorbitan monolaurate | 1.0 |
| | Preservative | 0.2 |
| | Perfume | 0.2 |
| Phase B | 1,3-Butylene glycol | 8.0 |
| | Purified Water | qs 100.0 |
| Phase C | Titanium oxide flakes | 5.0 |
| | UV-Powder 2000 | 2.0 |
| | Anhydrous silicon oxide | 0.2 |

Example 13 shown above can be prepared by any conventional method well known in the art, for example, the method described for Example 8.

The composition having the above formulation had an SPF value of 14.7, showing sunscreening effects, and exhibited satisfactory spreadability on the skin to give a natural makeup finish.

EXAMPLE 14

Sunscreening Oil

| COMPONENTS | | AMOUNT (%) |
|---|---|---|
| Phase A | Octyldimethyl p-aminobenzoate | 4.0 |
| | 4-t-Butyl-4'-methoxybenzoyl-methane | 1.0 |
| | Tocopherol acetate | 0.1 |
| Phase B | Perfume | adequate amount |
| | Volatile silicone | qs 100.0 |
| Phase C | Titanium oxide flakes | 10.0 |
| | UV-Powder 1010 | 1.0 |

Example 14 shown above can be prepared by any conventional method well known in the art, for example, the method described for Example 8.

The sunscreening oil having the above formulation had an SPF value of 17.5 showing sunscreening effects and exhibited a natural makeup finish and satisfactory spreadability on the skin.

EXAMPLE 15

Lip-Glow

| COMPONENTS | | AMOUNT (%) |
|---|---|---|
| Phase A | Carnauba wax | 4.5 |
| | Candelilla wax | 9.0 |
| | Ceresin | 2.5 |
| | Bleached bees wax | 1.5 |
| | Cocoa butter | 4.0 |
| | Sucrose fatty acid esters | 2.0 |
| | Lanolin | 20.0 |
| | Liquid paraffin | qs 100.0 |
| | Antioxidant | adequate amount |
| Phase B | Allantoin | adequate amount |
| | Titanium oxide flakes | 5.0 |
| | UV-Powder 2000 | 5.0 |
| | Red No. 3 aluminum flakes | adequate amount |
| | Perfume | adequate amount |

Example 15 shown above can be prepared by any conventional method well known in the art. A suitable method is as follows:

Components of Phase A are homogeneously melted at 80°–90° C., and components of Phase B except perfume under stirring with a daysolver. The obtained melt is thoroughly stirred, allowed to stand for degassing, cooled to 65°–70° C., and perfume is added. The finally obtained melt is gently stirred, and molded into a stick.

The lip-glow having the above formulation had an SPF value of 15.6, showing sunscreening effects, and exhibited a natural makeup finish and satisfactory spreadability on the skin.

The cosmetics according to the present invention not only produce excellent effects of protecting the skin from harmful ultraviolet rays as can be seen from the SPF values obtained in the foregoing Examples but also have safety, satisfactory utility, and satisfactory makeup finishes. They are valuable cosmetics which give a natural finish when used on the skin.

What is claimed is:

1. A sunscreening cosmetic composition for application to skin comprising:
   (a) an effective amount of a metal oxide flake having a thickness of from about 0.01 to about 3 μm and an average size of from about 1 to about 100 μm; and
   (b) an effective amount of a ultraviolet absorbent-encapsulated polymer resin particle obtained by polymerizing a monomer of the polymer resin uniformly mixed with the ultraviolet absorbent.

2. The cosmetic composition according to claim 1, the balance of which comprises a cosmetically-acceptable topical carder.

3. The cosmetic composition according to claim 2 wherein said ultraviolet absorbent-encapsulated polymer resin particle has a structure wherein the polymer resin membrane encapsulates a core comprising the ultraviolet absorbent.

4. The cosmetic composition according to claim 1 wherein said composition comprises from about 1% to about 70% of said metal oxide flakes.

5. The cosmetic composition according to claim 4 wherein said composition comprises from about 0.1% to about 70% of said ultraviolet absorbent-encapsulated polymer resin particle.

6. The cosmetic composition according to claim 5 wherein said ultraviolet absorbent-encapsulated polymer resin particle contains from about 1% to about 50% of said ultraviolet absorbent.

7. The cosmetic composition according to claim 6 wherein said polymer resin is selected from the group consisting of vinyl polymers, olefin-vinyl polymers, olefin-alkyl polymers, polyamides, acrylic resins, polystyrene, polyesters, and mixtures thereof.

8. The cosmetic composition according to claim 7 wherein said ultraviolet absorbent is selected from the group consisting of aminobenzoic acid and derivatives thereof, salicylic acid and derivatives thereof, cinnamic acid and derivatives thereof, benzophenone derivatives, urocanic acid and derivatives thereof, and mixtures thereof.

9. The cosmetic composition according to claim 8 wherein said ultraviolet absorbent is selected from the group consisting of 2-hydroxy-4-methoxybenzophenone, 2-hydroxy-4-methoxybenzophenone-5-sulfonic acid, 2,2'-dihydroxy-4-methoxybenzophenone, diethanolamine p-methoxyhydrocinnamate, ethyl-dihydroxypropyl p-aminobenzoate, glyceryl p-aminobenzoate, homomethyl salicylate, methyl o-amino-benzoate, 2-ethylhexyl-2-cyano-3,3-diphenyl-acrylate, octyldimethyl p-aminobenzoate acid, 2-ethylhexy-p-methoxycinnamic acid, 2-ethylhexylsalicylic acid, p-amino-benzoic acid, 2-phenylbenzimidazoyl-5-sulfonic acid, triethanolamine salicylate, 3-(4-methylbenzylidene)-camphor, 2,4-dihydroxybenzophenone, 2,2',4'4,-tetrahydroxybenzophenone, 2,2'-dihydroxy-4,4'-dimethoxybenzophenone, octabenzone. 4-isopropyldibenzoylmethane, 4-t-butyl-4'-methoxybenzoyl-methane, 2-ethyl-2-cyano 3,3'-diphenylacrylate, urocanic acid, ethyl urocanate, and mixtures thereof.

10. The cosmetic composition according to claim 8 wherein said metal oxide flakes are selected from the group consisting of zinc oxide, titanium oxide, zirconium oxide, and mixtures thereof.

11. The cosmetic composition according to claim 10 wherein said ultraviolet absorbent-encapsulated polymer resin particle has a size of from about 5 μm to about 20 μm.

12. The cosmetic composition according to claim 10 wherein, in said ultraviolet absorbent-encapsulated polymer resin particle, said polymer resin is polymethyl methacrylate and said ultraviolet absorbent is selected from the group consisting of octyldimethyl-p-aminobenzoate 4-t-butyl-4'-methoxybenzoylmethane, and mixtures thereof.

13. A method of providing cosmetic and sunscreening benefits to the skin by applying to the skin an effective amount of the cosmetic composition according to claim 5.

14. A method of providing cosmetic and sunscreen benefits to the skin by applying to the skin an effective amount of the cosmetic composition according to claim 10.

* * * * *

UNITED STATES PATENT AND TRADEMARK OFFICE
CERTIFICATE OF CORRECTION

PATENT NO. : 5,585,090

DATED : December 17, 1996

INVENTOR(S) : Yoshioka et al.

It is certified that error appears in the above-identified patent and that said Letters Patent is hereby corrected as shown below:

Column 5, line 44, missing text after incorporated hereby by" should read --reference. Of course, the nature and--.
Column 6, line 29, "pads" should read --parts--.
Column 6, line 30, "pads" should read --parts--.
Column 6, line 31, "pads" should read --parts--.
Column 6, line 51, "pads" should read --parts--.
Column 6, line 52, "pads" should read --parts--.
Column 14, line 59, "carder" should read --carrier--.

Signed and Sealed this

Second Day of June, 1998

Attest:

BRUCE LEHMAN

*Attesting Officer*    Commissioner of Patents and Trademarks